(12) United States Patent
Rolnick et al.

(10) Patent No.: US 8,038,634 B2
(45) Date of Patent: *Oct. 18, 2011

(54) STERNOTOMY SPLINTING ASSEMBLY, KIT AND METHOD FOR USE

(76) Inventors: Michael A. Rolnick, Ellicott City, MD (US); Matthew P. Warden, Boston, MA (US); Robert A. Van Wyk, Largo, FL (US)

( * ) Notice: Subject to any disclaimer, the term of this patent is extended or adjusted under 35 U.S.C. 154(b) by 188 days.

This patent is subject to a terminal disclaimer.

(21) Appl. No.: 12/341,546

(22) Filed: Dec. 22, 2008

(65) Prior Publication Data

US 2009/0163949 A1 Jun. 25, 2009

Related U.S. Application Data

(60) Provisional application No. 61/008,764, filed on Dec. 21, 2007.

(51) Int. Cl.
*A61F 5/00* (2006.01)
*A61B 17/84* (2006.01)

(52) U.S. Cl. .................... 602/12; 606/300; 607/902

(58) Field of Classification Search ............... 602/5, 6, 602/7, 12, 14, 19, 20, 60, 70, 71; 600/459, 600/304, 453, 588, 300, 407, 437, 454, 456, 600/586; 607/902; 128/870, 876

See application file for complete search history.

(56) References Cited

U.S. PATENT DOCUMENTS

| | | | |
|---|---|---|---|
| 2,541,487 A | 2/1951 | Triplett | |
| 2,923,664 A | 2/1960 | Cook et al. | |
| 3,400,710 A | 9/1968 | Goldstein | |
| 3,561,436 A | 2/1971 | Gaylord et al. | |
| 4,680,020 A | 7/1987 | Kennedy et al. | |
| 4,732,146 A | 3/1988 | Fasline et al. | 128/55 |
| 4,825,866 A | 5/1989 | Pierce | 128/335 |
| 5,234,462 A * | 8/1993 | Pavletic | 606/215 |
| 5,437,623 A | 8/1995 | McClees et al. | 602/59 |
| 5,843,025 A | 12/1998 | Shaari | 602/53 |
| 6,570,051 B1 | 5/2003 | Beaudry | 602/54 |
| 6,971,995 B2 * | 12/2005 | Rolnick et al. | 602/12 |
| 7,198,609 B2 * | 4/2007 | Rolnick et al. | 602/12 |

OTHER PUBLICATIONS

"CardioThoracic Bra" and "CardioThoracic Harness" by Aztech Heart Inc. (2009).
"Heart Hugger Sternum Support Harness" by Heart Hugger, Inc. (2009).

* cited by examiner

*Primary Examiner* — Patricia Bianco
*Assistant Examiner* — Tarla Patel
(74) *Attorney, Agent, or Firm* — Chalin Smith; Smith Patent Consulting

(57) ABSTRACT

Herein disclosed is a simple, passive splinting system for sternotomy patients designed to provide a continuous yet readily adjustable, compressive tangential stabilizing force to the ribcage so as to promote healing of a median sternotomy incision while minimizing patient pain.

17 Claims, 12 Drawing Sheets

(a)

(b)

(a)

(b)

(c)

STERNOTOMY SPLINTING ASSEMBLY, KIT AND METHOD FOR USE

PRIORITY

This application claims the benefit of U.S. Provisional Application No. 61/008,764 filed Dec. 21, 2007, the entire contents of which are incorporated by reference herein.

FIELD OF THE INVENTION

The present invention relates to a splinting assembly, kit and method. More particularly, the present invention relates to an assembly, method and kit for splinting a median sternotomy incision on a patient post-surgery.

BACKGROUND OF THE INVENTION

Patients undergo chest surgery for a variety of reasons including coronary artery bypass, tumor removal, lung and heart transplants. While it is sometimes possible to use less invasive surgical techniques, many of these procedures require gaining access by opening up the chest at the breastbone. There are three basic incisions used to gain access: full sternotomy, partial sternotomy and thoracotomy. The type of incision used depends on the procedure and the general health of the patient. The most common incision is a full sternotomy. During a full sternotomy, the surgeon makes an incision down the center of the chest. The breastbone is divided and held open with a device called a retractor. When the surgery is completed, the doctor reattaches the breastbone with stainless steel wire and sutures the skin. The incision is covered with sterile dressings.

This sternum functions as the anterior stabilizing force for all of the ribs. As a result, a sternotomy destabilizes the previously closed circle of the ribs, thoracic spine, and the sternum. There is significant pain associated with sternal healing.

Care of the lungs is important in order to avoid pneumonia following any surgical procedure involving anesthesia. It is especially important following heart surgery. The surgery itself sometimes involves the lungs or the sacs around the lungs. In addition, if a patient is on the Heart-Lung Machine, the lungs are deflated during the surgery. This frequently causes lungs to create more mucous, making the small air sacs on the outside of the lungs more easily closed. Accordingly, coughing and deep breathing are often necessary during recovery to open the small airsacs and to remove the extra mucous. If the airsacs stay closed and mucous builds up, pneumonia can easily develop. The necessary coughing and deep breathing are frequently very painful following sternotomy.

Sternal pain during coughing and deep breathing may be decreased by splinting the site. Most commonly, the patient hugs a pillow, folded blanket or towel or similar to the chest during deep breathing or coughing so as to apply a compressive force to the site. While somewhat effective in reducing pain, it is suboptimal since the force is applied normal to the sternum and does not decrease the tangential (separating) force on the healing sternum.

Other splinting devices are presently available for decreasing the separation force on the sternum during coughing and deep breathing. The "Cardiothoracic Harness" and "Cardiothoracic Bra" by AztecHeart, Inc. (Oroville, Calif.) are two circumferential devices which stabilize the chest of patients following sternotomy. However, these devices are overly complex and can be painful to apply and adjust on patients who are elderly, obese or have dementia. The "Heart Hugger™" sternotomy support harness by Heart Hugger, Inc. (Los Gatos, Calif.) is a circumferential device which is not closed in the front, but rather has a handle portion attached to the circumferential strap on each side of the frontal gap. However, this device too is deficient as the tangential force is not applied to the ribcage continuously but rather is applied by the patient as necessary, by pulling the handle portions toward each other so as to decrease the frontal gap. The device is well suited to patients with good arm strength, but may not be suitable for patients who are obese, elderly, have dementia, or are incapable of grasping and applying force to the handle portions.

Thus, there is a remaining need in the art for a simple, passive splinting system for median sternotomy patients.

SUMMARY OF THE INVENTION

It is accordingly an object of the present invention to provide an assembly, kit, and method for splinting a sternotomy that is capable of providing a continuous yet readily adjustable, compressive tangential stabilizing force to the ribcage to promote healing while minimizing patient pain. In particular, the sternotomy splinting assembly of the present invention utilizes two anchor patches placed on the chest wall approximately equidistant from the sternotomy incision site, in a more or less vertical orientation, and a series of elastomeric straps placed across the site, horizontally so as to produce a stabilizing force on the site.

In a preferred embodiment, the elastomeric straps may be removably affixed to the anchor patches by means of mating fastening components, such as hook and loop fasteners. During placement, an initial tension is supplied to the elastomeric straps. In this manner, a reducing force is produced across the site regardless of the degree of chest expansion, the reducing force increasing with increasing expansion of the chest. The rate of increase in the reducing force as a function of degree of chest expansion is determined by the spring-constant of the elastomeric strap. Elastomeric straps having a low spring-constant will provide less increase in the reducing force with increased chest expansion than elastomeric straps having a higher spring-constant. By choosing the proper combination of elastomeric strap spring-constant and initial tension in the strap, a reducing force profile may be created which provides maximum patient comfort. The present invention contemplates the use of elastomeric straps with spring constants varying from very low (for instance, for pediatric applications) to extremely high.

In preferred embodiment, the elastomeric straps may be removed and reapplied, their placement and the amount of initial tension being adjustable so as to maximize patient comfort. Tension in the elastomeric straps may be reduced by the patient by unfastening one end from its anchor strip.

In a further preferred embodiment, a pad may be placed between the elastomeric straps and the chest wall so as to produce a force normal to the chest wall at the sternotomy site. The pad may be heated or cooled as needed.

The present invention also provides a kit containing the requisite elements needed to splint a sternotomy incision in accordance with the principles of this invention. In a preferred embodiment, the elements of the kit include (i) anchor patches, (ii) a means for optimally positioning the patches on a patient, (iii) adhesive, and (iv) elastomeric straps. In one preferred embodiment, the adhesive separate from the anchor patches and is applied to the patches and/or patient using a template which also acts as a positioning device. In an alternate preferred embodiment, the adhesive is pre-applied to the anchor patches during manufacture and the positioning device is a strip which optimally spaces and centers the patches on the patient. The kits may optionally also include a solvent to aid in the removal of the anchor patches, gauze pads to apply solvent and/or wash the affected area, instructions for splinting a median sternotomy using the kit components and/ or a compressive pad for placement on the chest wall at the sternotomy site.

It will be understood by those skilled in the art that one or more aspects of this invention can meet certain objectives, while one or more other aspects can meet certain other objectives. Each objective may not apply equally, in all its respects, to every aspect of this invention. As such, the preceding objectives should be viewed in the alternative with respect to any one aspect of this invention.

Additional features of the invention will become more fully apparent when the following detailed description is read in conjunction with the accompanying figures and/or examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of electrode design. Such objects, features, benefits and advantages will be apparent from the above in conjunction with the accompanying examples, data, figures and all reasonable inferences to be drawn there-from, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

FIG. 2a depicts a plan view of an illustrative elastomeric strap suitable for use in conjunction with the sternotomy splint assembly of the present invention.

FIG. 2b is a side elevational view of the object of FIG. 2a.

DETAILED DESCRIPTION OF THE PREFERRED EMBODIMENTS

This present invention constitutes a marked improvement in the field of sternotomy splinting by providing simple, passive system for sternotomy patients that is capable of providing a continuous tangential stabilizing force to the ribcage to enhance healing while minimizing patient pain.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

In the context of the present invention, the words "a", "an", and "the" as used herein mean "at least one" unless otherwise specifically indicated.

In the context of the present invention, the side of a component that faces away from the patient is referred to in the alternative as the "upper surface", the "top surface", and the "obverse surface". In a similar fashion, the side of a component of the present invention that contacts the patient is referred to in the alternative as the "lower surface", the "bottom surface", and the "reverse surface".

Unless otherwise defined, all technical and scientific terms used herein have the same meaning as commonly understood by one of ordinary skill in the art to which this invention belongs. In case of conflict, the present specification, including definitions, will control.

EXAMPLES

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Figure 1:
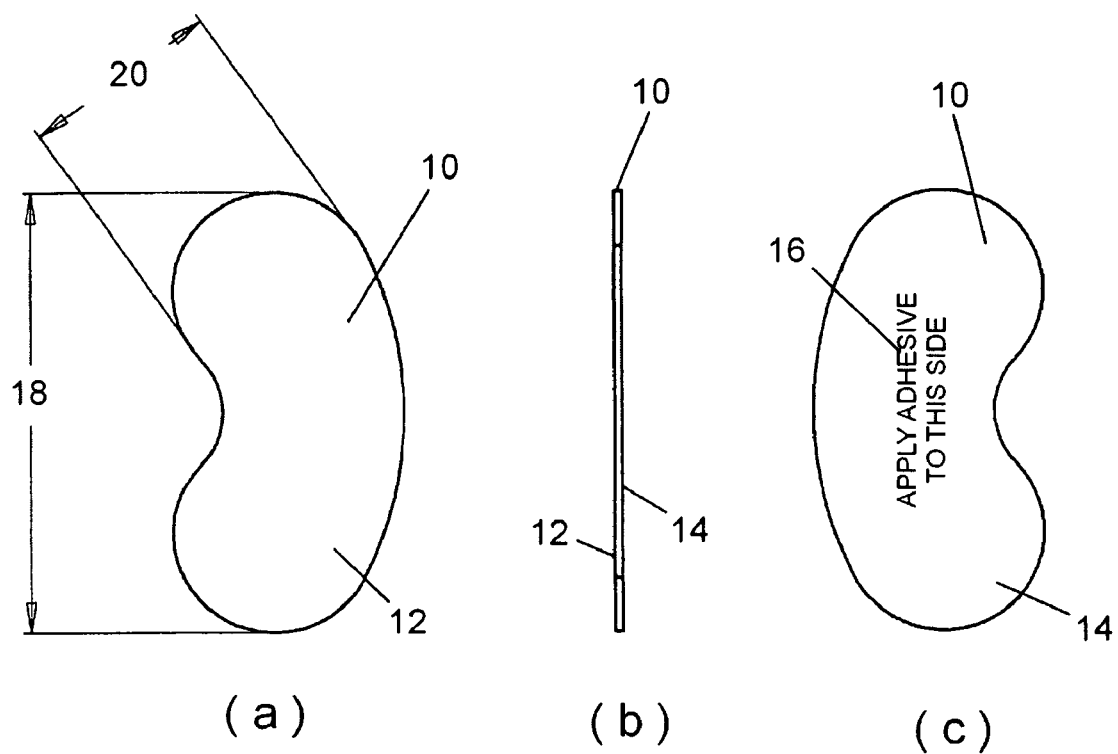
FIG. 1a depicts a plan view showing a first (top, obverse) surface of an anchor patch suitable for use in conjunction with the sternotomy splint assembly of the present invention.
FIG. 1b depicts the object of FIG. 1a in edge view
FIG. 1c depicts a plan view of the object of FIG. 1a showing a second (bottom, reverse) surface.

Referring now to the figures, FIGS. 1a through 1c depict a first embodiment of an anchor patch 10 suitable for use in conjunction with a sternotomy splinting system of the present invention. Patch 10 has a first side 12, an obverse surface, having formed thereon hooks or hook protrusions suitable for forming a hook and loop fastener pair, and a second side 14, a reverse surface, having an indicia 16 formed thereon, indicia 16 indicating that second side 14 is the side to which adhesive should be applied. Patch 10 has a contoured or curvilinear shape, the length 18 of patch 10 preferably between about 4 and 12 inches, and more preferably between about 4 and 8 inches. Width 20 of patch 10 is preferably between about one and five inches and more preferably between about 1½ and 4 inches. In other embodiments, patch 10 has other shapes including circular, ovoid, rectangular, having a perimeter that is curvilinear, linear, or a combinations thereof.

Anchor patch 10 is preferably incorporates a low-profile hook material having a shear strength sufficient to maintain integrity of the fastener pair during use, but with a low peel strength which allows easy removal of an elastic strap from the patch during use. Additionally, the hook material should be soft and compliant so that the patch can conform to the contours of the chest wall during use. Height of the hooks is preferably less than about 0.035 inches and more preferably less than 0.025 inches.

FIGS. 2a and 2b depict a first embodiment an elastomeric strap suitable for use in conjunction with a sternotomy splinting system of the present invention. Strap 30 has a first relative smooth side (the obverse side) and a second reverse die 32 onto which are affixed loop or pile pad portions 34 at its ends, such portions 34 being suitable for forming a fastener pair with the hooks of first side 12 of anchor patch 10. Elastomeric strap 30 is formed from a suitable elastomeric material. In a preferred embodiment, strap 30 is formed from ribbed, non-roll elastomeric fabric having about 88% polyester and about 12% rubber content. In other embodiments, other elastomeric materials may be used. Unconstrained length 36 of strap 30 is preferably between about 4 and 12 inches, and more preferably between about 5 and 10 inches. Width 38 of strap 30 is preferably between about 1 and 4 inches and more preferably between about 1½ and 3 inches.

Figure 3:
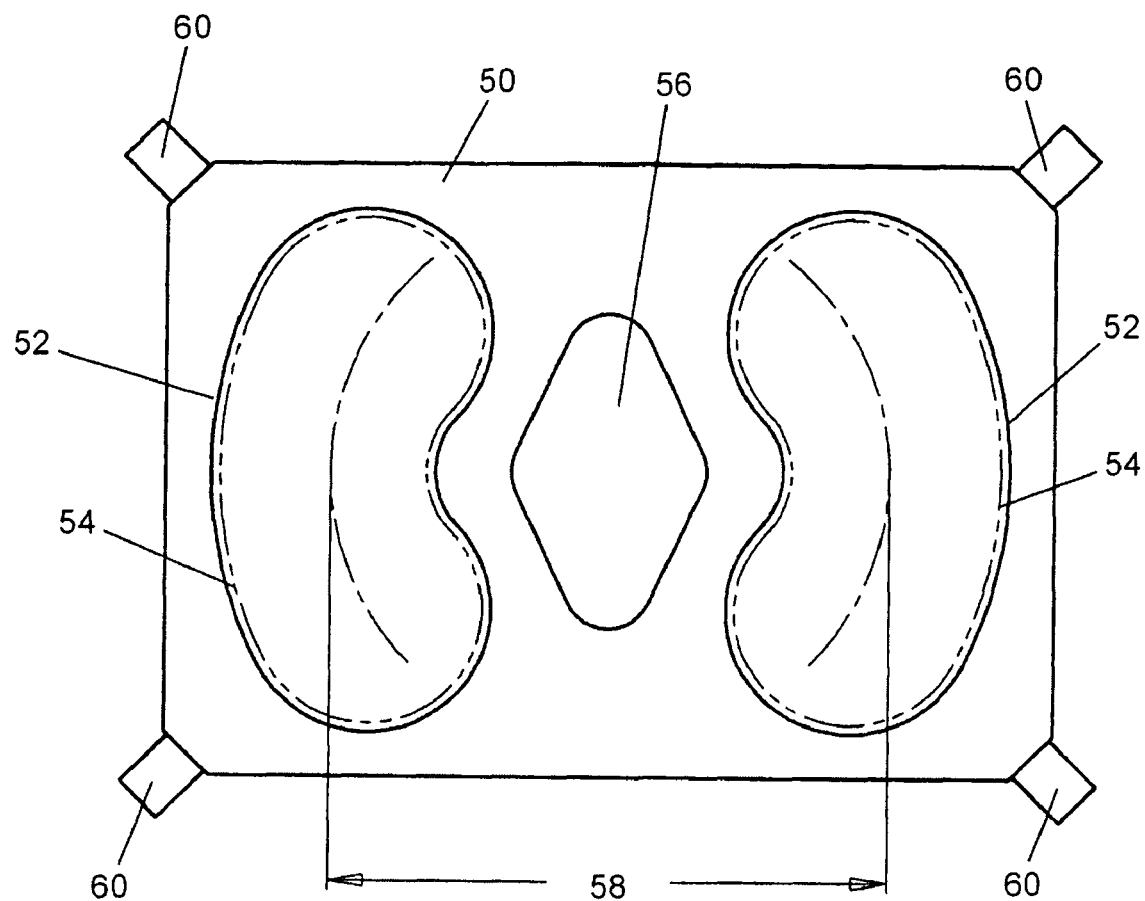
FIG. 3 depicts a locating template that may be used to position the anchor patches of FIG. 1 on a sternotomy patient.

FIG. 3 depicts an exemplary locating template 50 suitable for use in placing and positioning a sternotomy splinting assembly formed in accordance with the principles of this invention. In a preferred embodiment, template 50 is formed from a semi-rigid paper such as 110# card stock. In other embodiments template 50 is formed from coated or uncoated paper, fabric or other sheet material. Template 50 has formed therein cut outs or openings 52 complimentary to the shape 54 of anchor patch 10, openings 52 being slightly larger. In a preferred embodiment, openings 52 are about 0.1 inches per side larger than shape 54. Template 50 also has formed therein opening 56 centered between openings 52. Openings 52 are spaced distance 58 apart, distance 58 being preferably between about 5 and 12 inches and more preferably between about 6 and 10 inches. Adhesive strips 60 are affixed to the template 50, preferably at one or more of the corners. Template 50 is depicted with a rectangular shape. Other shapes may be used including circular, oblong, or other irregular shapes provided that the shape includes opening 56 and openings 52, there being sufficient material between openings 52 and the perimeter of template 50 to prevent inadvertent application of adhesive to regions outside the perimeter of template 50.

The sternotomy splinting assembly herein disclosed applies a tangential stabilizing force on the sternum, the force being supplied by elastic straps 30 which are affixed to anchor patches 10 which are adhered to the chest wall, and which are positioned by template 50 so that straps 30 span the sternotomy incision site. In a preferred embodiment herein described, anchor patches 10 are adhered to the chest wall using a standard ostomy adhesive applied to patches 10 and the chest wall. The steps for applying the sternotomy splinting assembly are described below.

Figure 4:
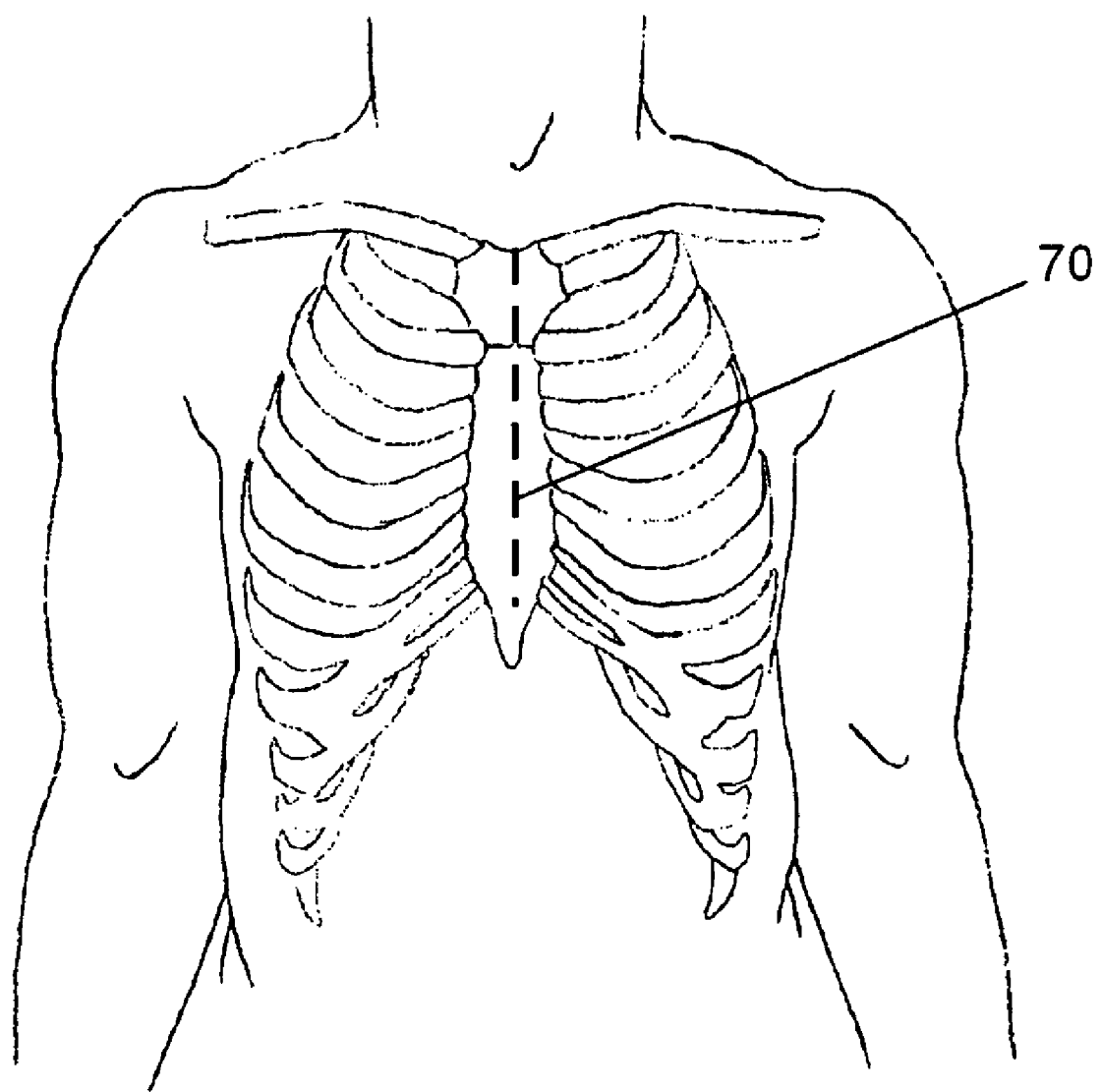
FIG. 4 depicts a sternotomy incision on a patient.
Figure 5:
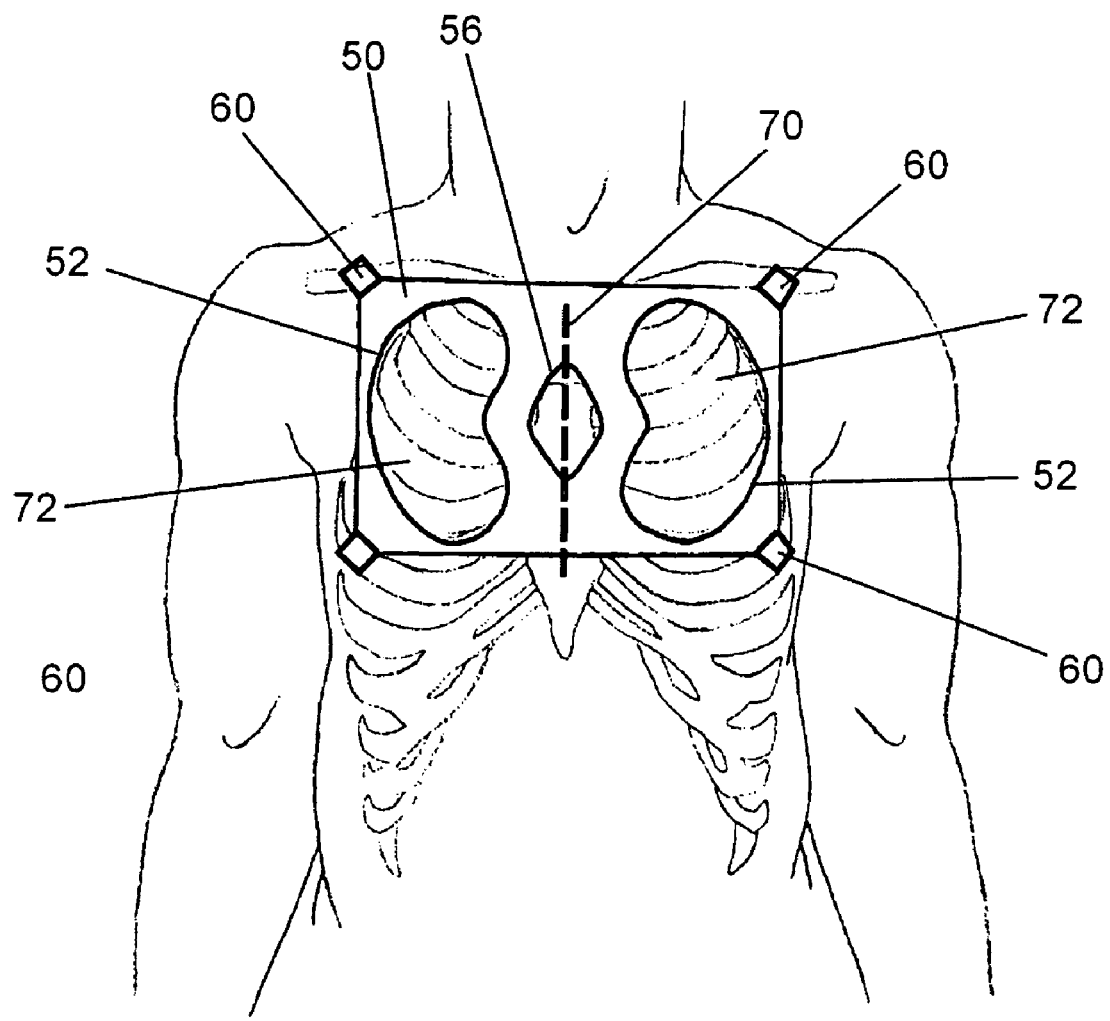
FIG. 5 depicts the locating template of FIG. 3 affixed to the patient of FIG. 4 in preparation for application of adhesive to the patient.

FIG. 4 depicts the anatomy of a patient with a sternotomy incision 70. FIG. 5 depicts template 50 removably affixed to the chest wall by adhesive strips 60. In other embodiments, adhesive strips are not affixed to the template, and the template is retained in position on the patient using adhesive tape supplied by the hospital. A suitable adhesive is applied to regions 72 of the chest wall, regions 72 being those exposed by openings 52 of template 50. Template 50 is centered on sternotomy 70 using opening 56. Template 50 serves two functions: establishing the locations to which anchor patches 10 will be adhered, and limiting the area to which adhesive is applied to only that required to adhere anchor patches 10 to the chest wall.

Figure 6:
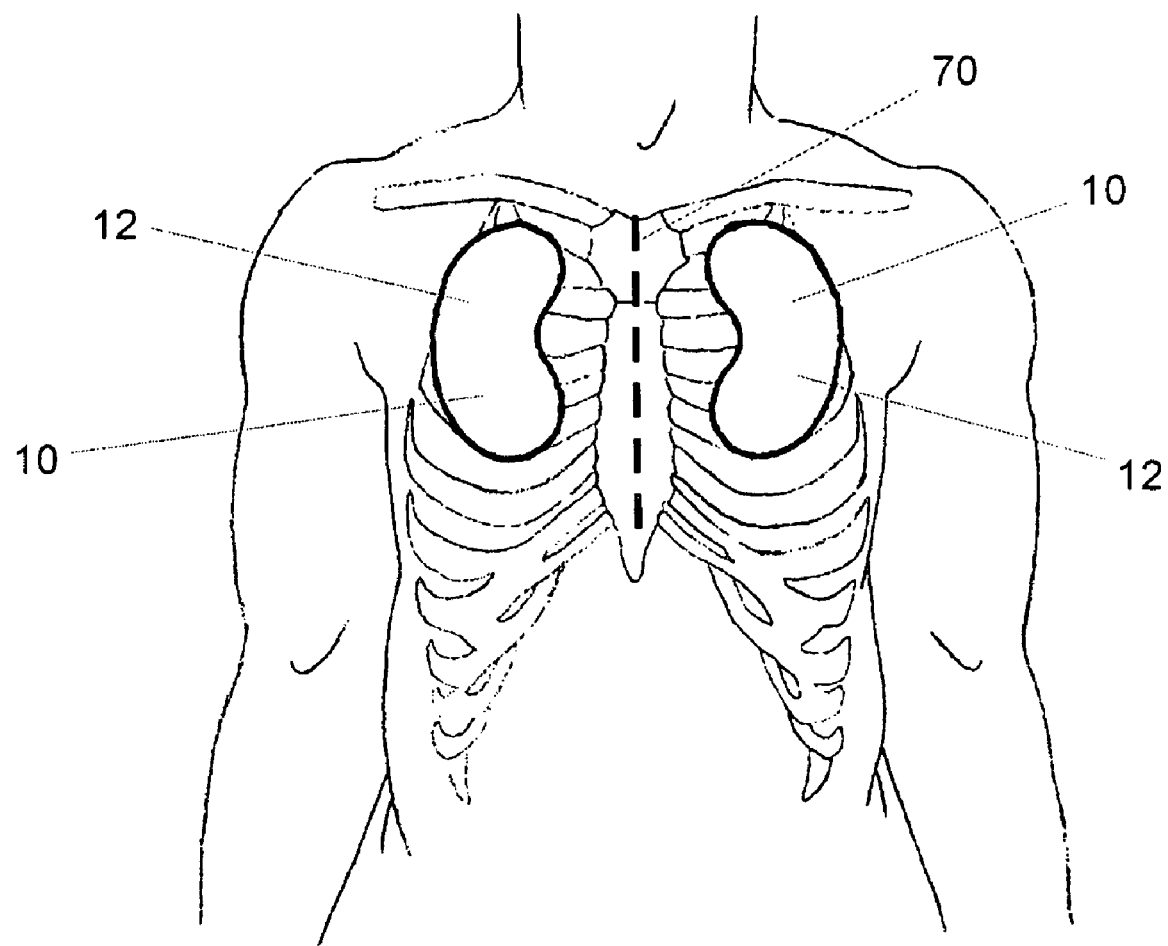
FIG. 6 depicts the anchor patches of FIG. 1 affixed to the patient of FIG. 4.

Adhesive is also applied to second sides 14 of patches 10. In a preferred embodiment a standard ostomy adhesive such as Nu-Hope™ Adhesive from Nu-Hope Labs (Pacoima, Calif.) is used. The adhesive is allowed to dry for about five minutes, following which the anchor patches 10 are applied to the chest wall as shown in FIG. 6. First (obverse) surfaces 12 of anchor patches 10, forming the hook portions of a hook and loop fastener pair, are exposed.

Figure 7:
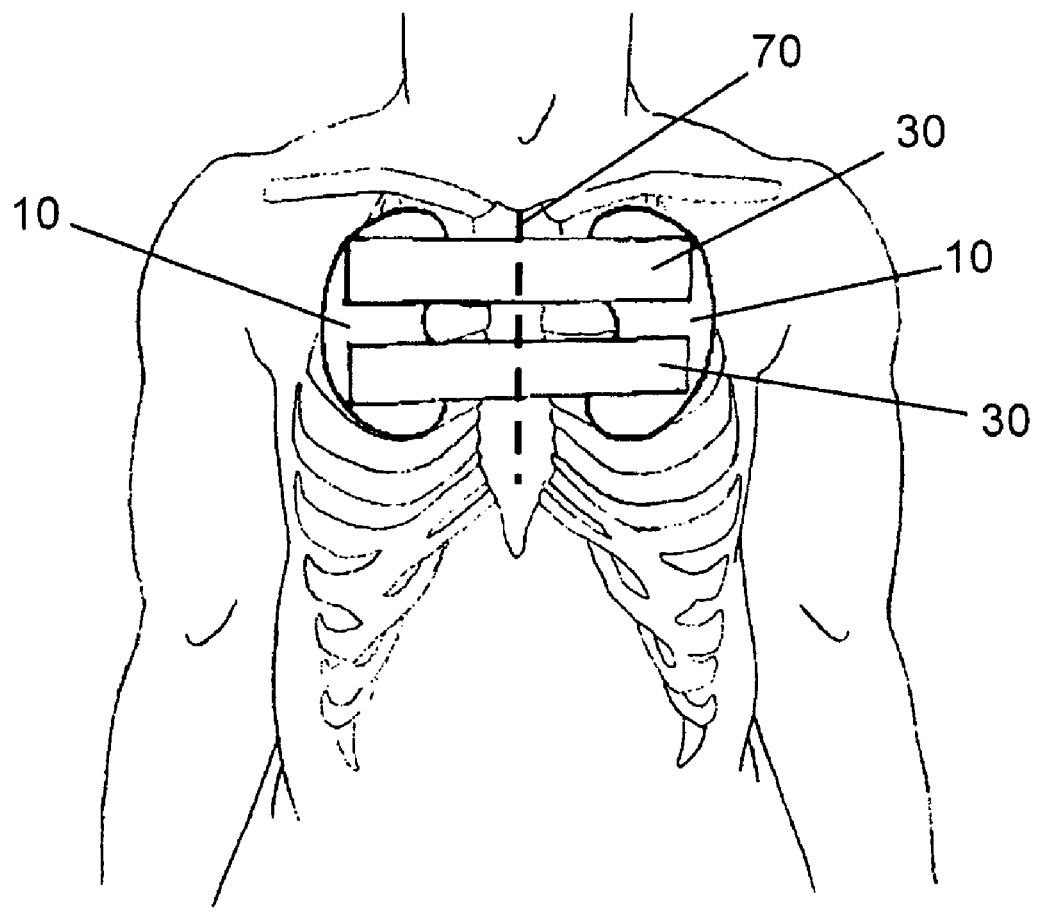
FIG. 7 depicts the sternotomy splinting assembly in use on the patient of FIG. 4.

FIG. 7 depicts a sternotomy splinting assembly of the present invention in use on a patient. Elastomeric straps 30 may be removably affixed to anchor patches 10 by fastener pairs formed by hooks on first surface 12 of patches 10 and loop or pile portions 34 on the second surface of elastomeric straps 30. In affixing straps 30 to patches 10, a first end of a strap 30 is affixed to a first patch 10. The strap 30 is then stretched and the second end of the strap 30 is affixed to the second patch 10. Tension in the straps 30 may be adjusted for maximum patient comfort and clinical effect.

To remove the splinting assembly, straps 30 are removed and discarded. Patches 10 may be removed using any suitable biocompatible solvent, preferably applied with gauze pads, following which the area is washed with soap and water to remove solvent residue.

In a preferred embodiment, two elastomeric straps 30 are used. In other embodiments, more straps 30 (e.g., at least three or more) may used, such as to splint large sternotomies. In addition, the strap width 38 may be reduced and a larger number of straps 30 used so as to distribute the force more evenly along anchor patches 10. The sternotomy splinting method is scalable so that it may be used to treat a range of patient sizes, including pediatric subjects.

In one preferred embodiment, an ostomy adhesive is applied to the chest wall and anchor patches 10. In an alternate preferred embodiment, a suitable adhesive may be applied to the anchor patches during manufacture and preferably covered with a release strip, so that application of adhesive during mounting of the splint on a patient is not required. In such an embodiment, template 50 may not be required, as positioning of the anchor patches on the patient may be accomplished using a locating strap fastened to the patches prior to mounting on the patient.

In a preferred embodiment, the adhesive has a high strength when loaded in shear (substantially tangential to the patient's body) but is easily removed by lifting of the edge of the anchor patch. Examples of such an adhesive are hydrocolloid adhesives and Foam Adhesive HT-513228 both available from Hi-Tech Products (Buena Park, Calif.). Other adhesives may also be used which require solvent for removal of the anchor patch. Such adhesives may be required to maintain sufficient bond strength when submerged in warm water as is required during water births.

Figure 8:
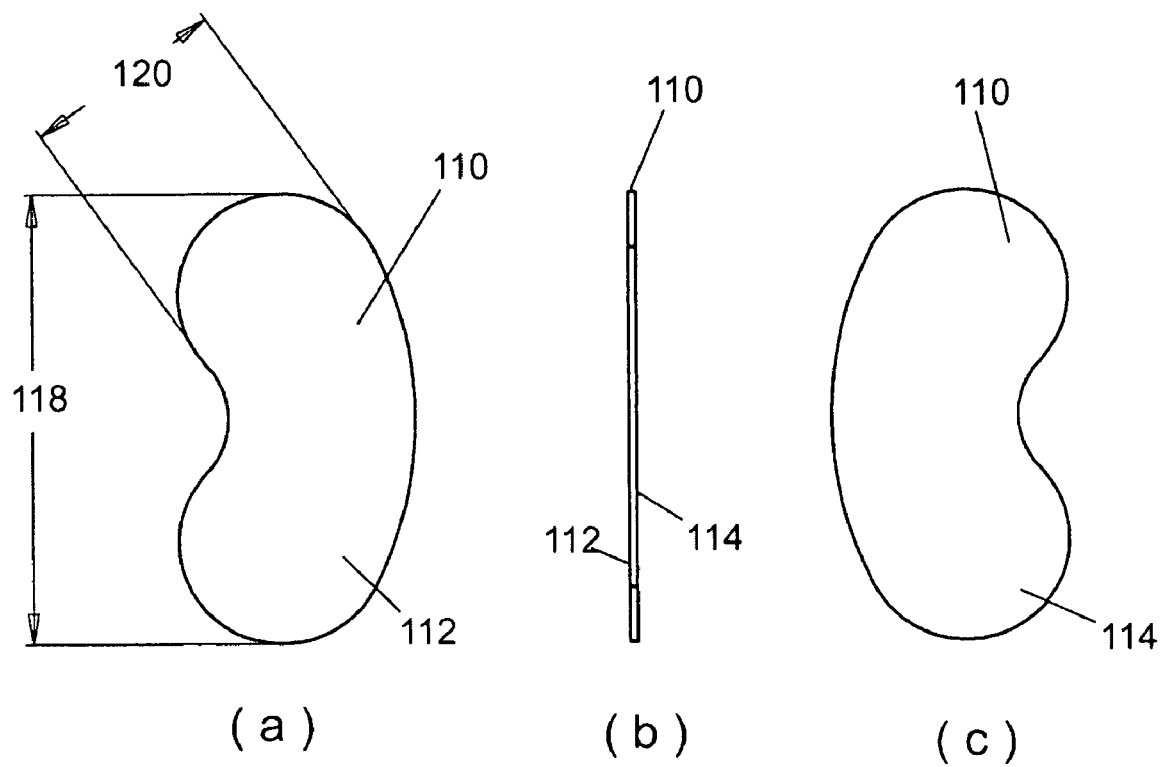
FIG. 8 depicts an alternate embodiment of an anchor patch suitable for use in conjunction with the sternotomy splinting assembly of the present invention.

Referring to FIGS. 8(a) through 8(c), anchor patch 110 is identical to patch 10 except that indicia 16 (FIG. 1c) is eliminated and second side 114 has applied thereto during manufacture a suitable adhesive. Optional release strip is not shown.

Figure 9:
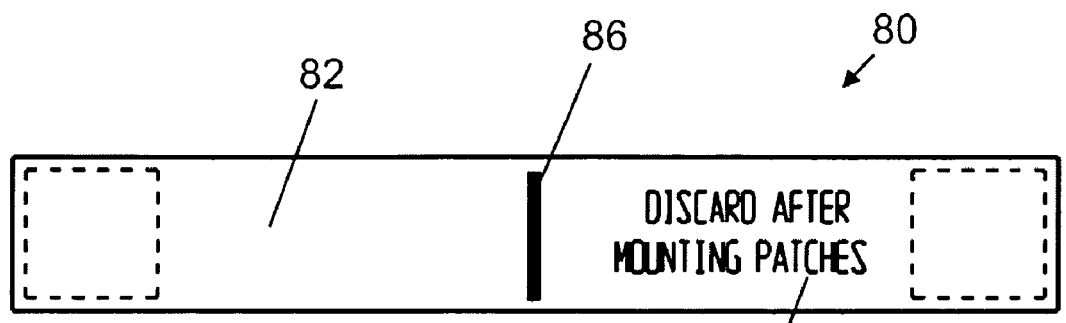
FIG. 9 depicts a locator strip suitable for use in conjunction with an alternate sternotomy splinting assembly of the present invention.
Figure 9:
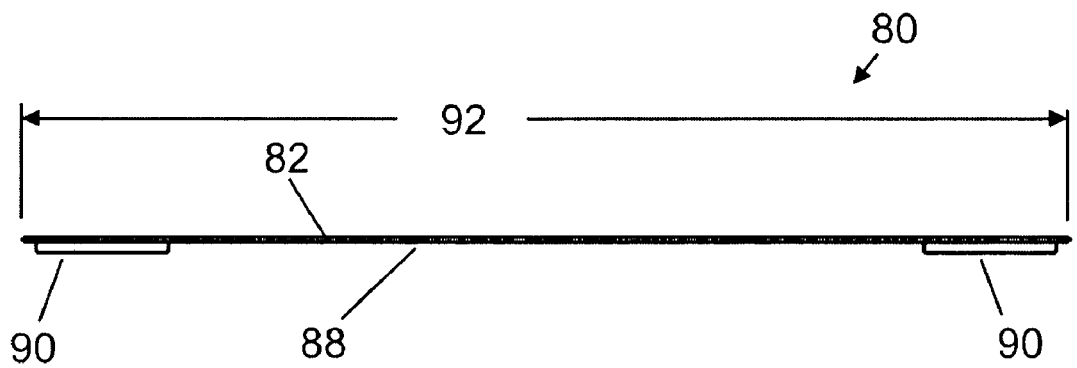
Figure 9:
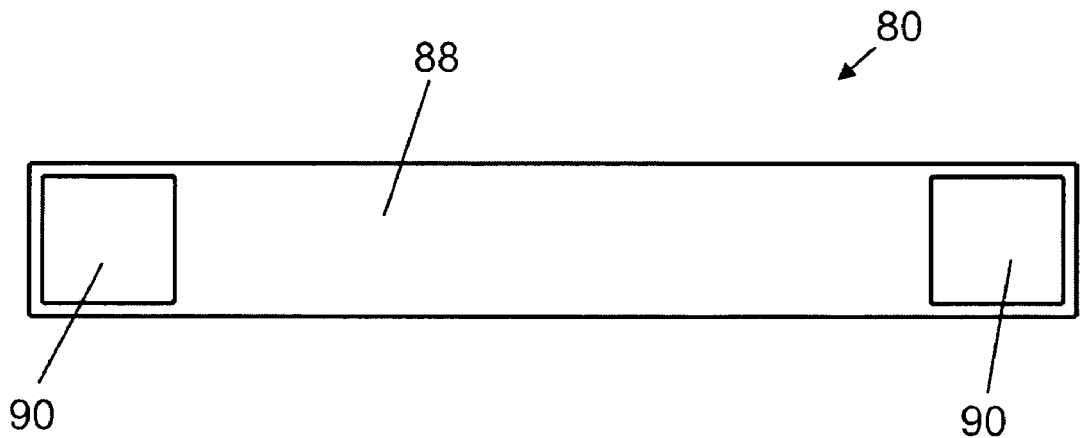

FIGS. 9(*a*) through 9(*c*) depict an optional locator strip suitable for use with anchor patches 110. Locator strip 80 has a first (obverse) side 82 having imprinted thereon indicia 84 and centering line 86 located equidistant from the strip ends. Second (reverse) side 88 has affixed thereto loop or pile portions 90 positioned adjacent to the ends of locator strip 80. Locator strip 80 has a predetermined length 92.

Figure 11:
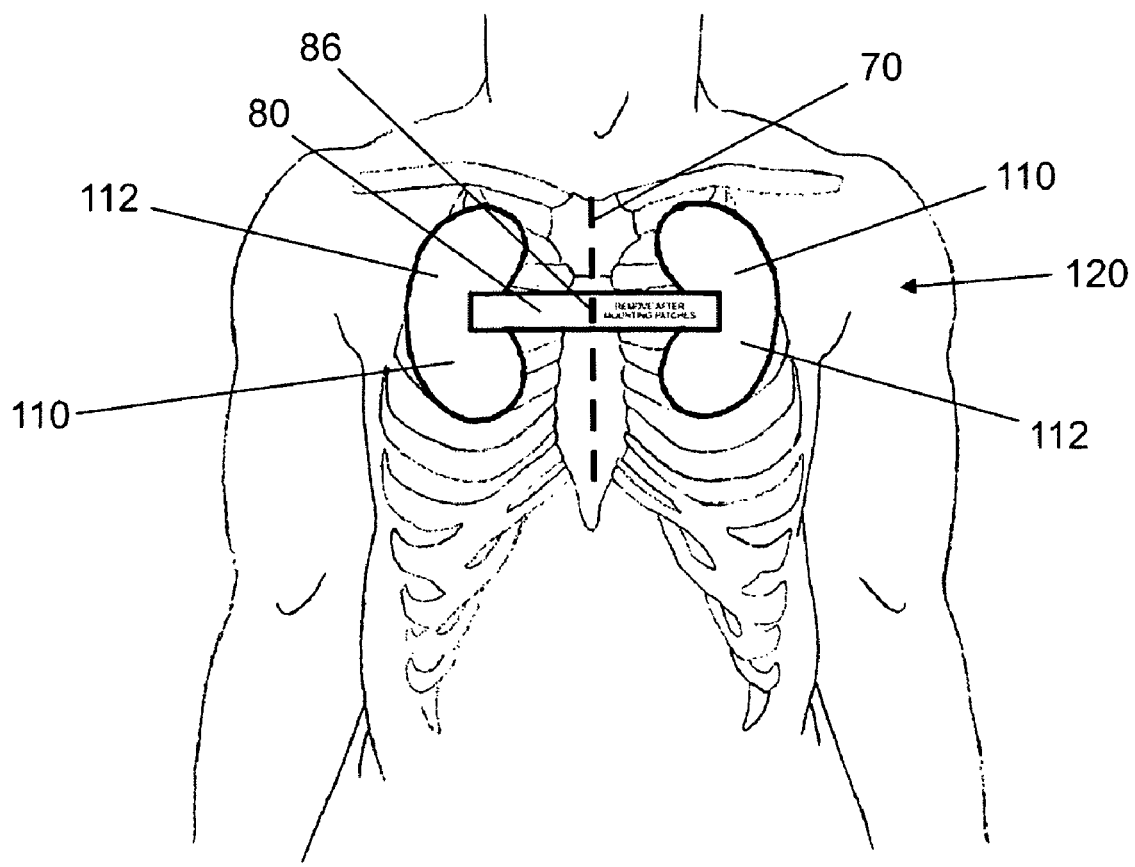
FIG. 11 depicts the assembly of FIG. 10 splinting a sternotomy incision.
Figure 12:
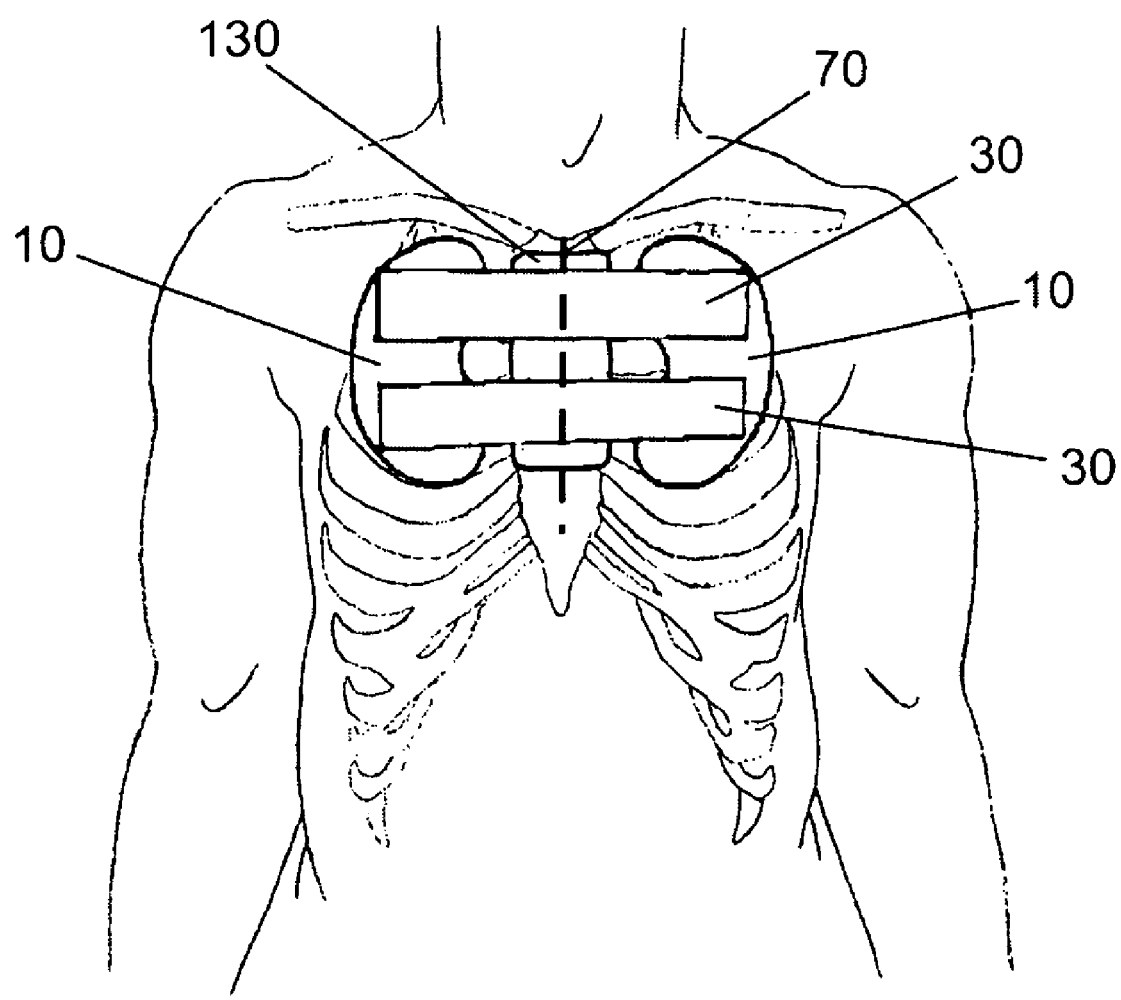
FIG. 12 depicts an alternate embodiment of the sternotomy splinting assembly of the present invention.

FIG. 11 depicts a sternotomy patient having assembly 120 mounted to the his chest. Centering line 86 is positioned at or over the sternotomy incision site so as to center assembly 120 and optimally position anchor patches 110. After the patches are mounted to the patient, locator strip 80 is removed. Application and tensioning of elastic straps 30 is accomplished in the same manner as in the previous embodiment.

Figure 2:
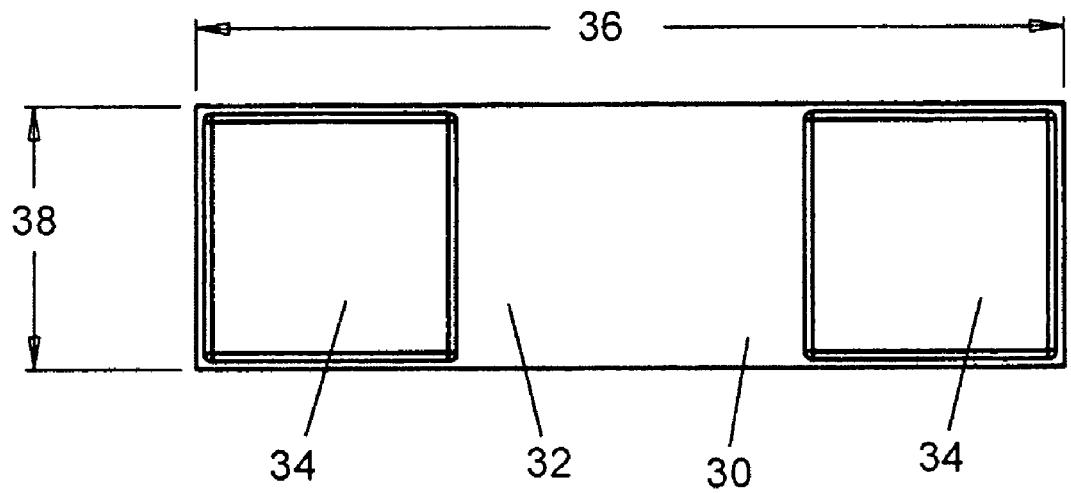
Figure 2:
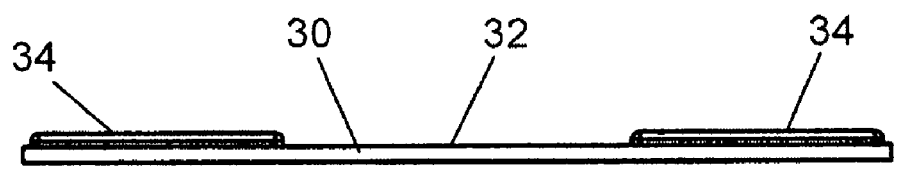
Figure 10:
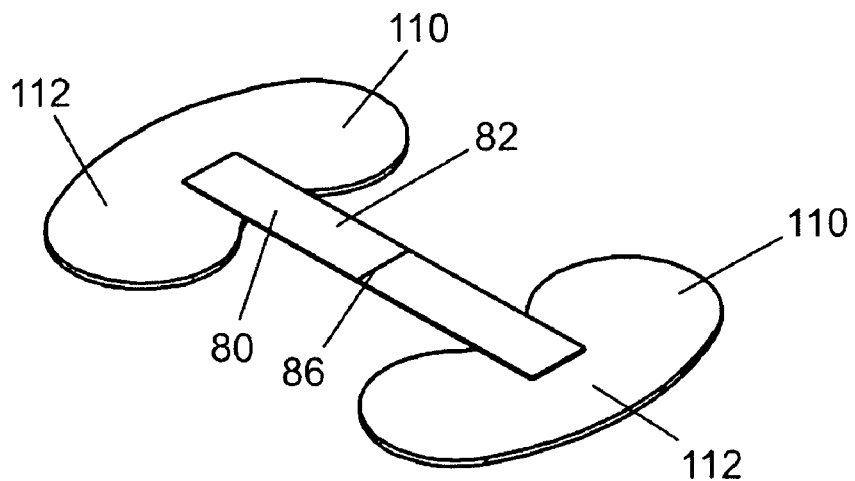
FIG. 10 depicts an assembly formed by anchor patches of FIG. 8 and the locator strip of FIG. 9.
Figure 10:
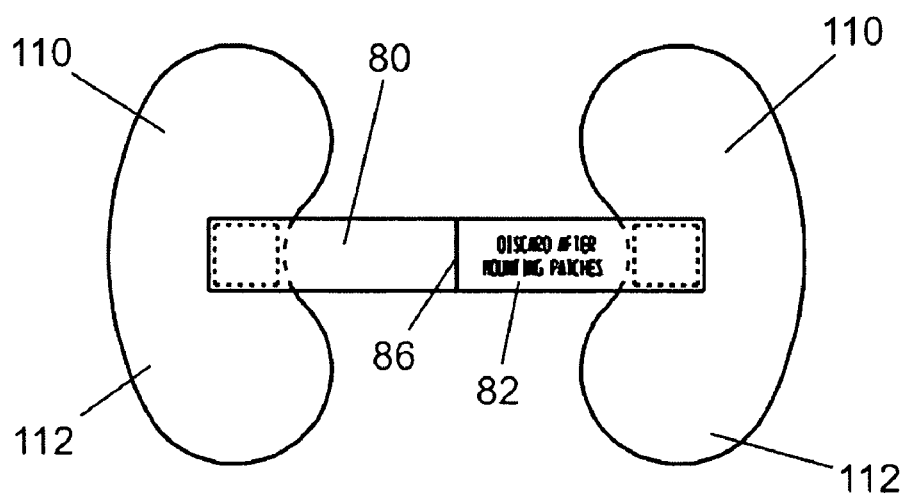
Figure 10:
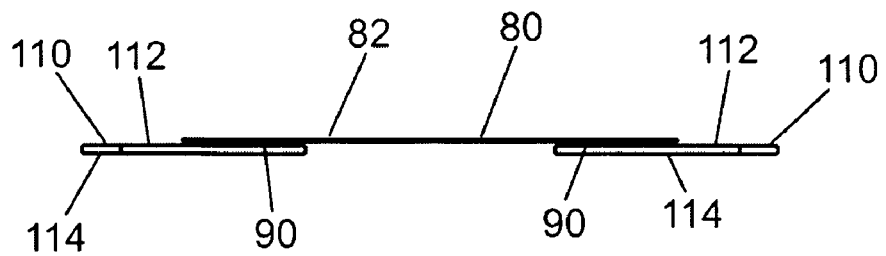

FIGS. 10(*a*) through 10(*c*) depict an assembly 120 formed by anchor patches 110 removably mounted to locator strip 80 in predetermined locations by fastener pairs formed by loop or pile portions 90 of locator strip 80 and hook portions of first (obverse) side 112 of patches 110. Length 92 of locator 80 and the predetermined mounting positions of locator 80 on patches 110 together relatively position patches 110 so that when the assembly is applied to a sternotomy patient the patches will be optimally positioned for splinting the injury with elastic straps 30 (FIG. 2).

In yet another embodiment, a small pad is inserted between straps 30 and the chest wall at the sternotomy site so as to produce a compressive, stabilizing force normal to the chest wall in additional to the tangential force.

In another aspect of the invention, a kit is disclosed, the kit containing anchor patches 10, elastomeric straps 30, positioning template 50, adhesive, removal solvent, and gauze pads. The kit may optionally further include instructions for splinting a median sternotomy using the kit components and/or a compressive pad for placement on the chest wall at the sternotomy site.

In still another aspect of the invention, a method for splinting a sternotomy is disclosed, the method including the steps of adhering anchor patches to the chest wall, and affixing at least one elastomeric strap between the patches so that the at least one elastomeric strap spans the sternotomy site.

INDUSTRIAL APPLICABILITY

The splinting assembly, kit and method present invention find utility in the area of median sternotomy repair. The assembly, kit and method of the present invention are designed to afford a compressive, tangential force to the septum to decrease the separation force on the sternum during the recovery period as well as during the requisite coughing and deep breathing exercises needed to open the small airsacs of the lung and prevent the onset of pathological pleural conditions post-surgery.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method for splinting a median sternotomy post-surgery using a splinting assembly comprising (a) two anchor strips having obverse and reverse surfaces, wherein the reverse surface is provided with either application instruction indicia or a pre-formed layer of adhesive covered with a release liner and the obverse surface is provided with a layer of a fastener receiving material, and (b) one or more elongate elastomeric straps having obverse and reverse surfaces and first and second ends, wherein the reverse surface of said one or more straps is provided at the respective first and second ends with a plurality of fasteners that mate with said fastener receiving material to form a releasable bond, said method comprising the steps of:
    a. adhesively mounting the two anchor strips more or less vertically at locations on the chest cavity of a median sternotomy patient that are more or less equidistantly displaced from the sternotomy site;
    b. attaching the fasteners disposed at a first end of said elastomeric strap to the layer of fastener receiving material disposed on one of anchor strips;
    c. stretching said at least one elastomeric strap so as to produce an initial tension in said at least one elastomeric strap, and
    d. coupling the fasteners disposed at the second end of said elastomeric strap to the layer of fastener receiving material disposed on the other of said anchor strips to thereby provide a compressive, stabilizing force tangential to the patient's sternum.

2. The method of claim 1 wherein said fastener receiving material comprises a plurality of hooks and said fasteners comprise a plurality of corresponding loops or pile portions, wherein said hooks and loops mate for form a fastener pair.

3. The method of claim 1, wherein said anchor strips are provided with a curvilinear perimeter that conforms to the contours of a chest wall.

4. The method of claim 1, wherein said anchor strips have a length of about 4 to 12 inches and a width of about 1 to 5 inches.

5. The method of claim 1, wherein said anchor strips have a length of about 4 to 8 inches and a width of about 1.5 to 4 inches.

6. The method of claim 1, wherein the reverse surfaces of said anchor strips are provided with a pre-formed layer of a high strength, biocompatible ostomy adhesive covered with a release liner.

7. The method of claim 1, wherein said assembly comprises at least two elastomeric straps mounted in parallel.

8. The method of claim 1, wherein said at least one elastomeric strap is formed from an elastomeric fabric comprising about 88% polyester and about 12% rubber.

9. The method of claim 1, wherein said at least one elastomeric strap has a length of about 4 to 12 inches and a width of about 1 to 4 inches.

10. The method of claim 1, wherein said at least one elastomeric strap has a length of about 5 to 10 inches and a width of about 1.5 to 3 inches.

11. The method of claim 1, further comprising the step of periodically adjusting the tension of said at least one elastomeric strap to maintain sufficient tension to provide patient comfort.

12. The method of claim 1, further comprising the steps of (i) initially positioning a relatively rectangular, semi-rigid locating template over the median sternotomy site, wherein said locating template comprises a first central opening that permits access to the site, a pair of cut-out openings complementary to the shape of said anchor patches located at either edge of the template, and one or more adhesive strips positioned about the perimeter of said template to permit releasable attachment to the chest wall of the sternotomy patient, and (ii) removing said locating template once said anchor strips are adhesively mounted in the proper position.

13. The method of claim 1 further comprising the steps of (a) providing an elongate locating strip having obverse and reverse surfaces and first and second ends, wherein the reverse surface of said locating strip is provided at the respective first and second ends with a plurality of fasteners that mate with said fastener receiving material on each of said anchor strips to form a releasable bond therewith and the obverse surface is provided with an indicia designating the center line of said locating strip; (b) positioning said locating strip and anchor strips across said median sternotomy such that said center line of said locating strip is positioned over the sternotomy site and said anchor strips are positioned at locations equidistant from said sternotomy site; and (c) removing said locating strips once said anchor strips are adhesively mounted in the proper position.

14. The method of claim 1, further comprising the step of placing a pad between said at least one elastomeric strap and the chest wall at the sternotomy site so as to produce a compressive, stabilizing force normal to the chest wall.

15. A kit for splinting a median sternotomy comprising:
a. two anchor strips having obverse and reverse surfaces, wherein the reverse surface is provided with either application instruction indicia or a pre-formed layer of adhesive covered with a release liner and the obverse surface is provided with a layer of a fastener receiving material;
b. one or more elongate elastomeric straps having obverse and reverse surfaces and first and second ends, wherein the reverse surface of said one or more straps is provided at the respective first and second ends with a plurality of fasteners that mate with said fastener receiving material to form a releasable bond;
c. a positioning means selected from (i) a semi-rigid locating template comprising a first central opening that permits access to the site of the median sternotomy, a pair of cut-out openings complementary to the shape of said anchor patches located at either edge of the template, and one or more adhesive strips positioned about the perimeter of said template to permit releasable attachment to the chest wall of the sternotomy patient, and (ii) an elongate locating strip having obverse and reverse surfaces and first and second ends, wherein the reverse surface of said locating strip is provided at the respective first and second ends with a plurality of fasteners that mate with said fastener receiving material on each of said anchor strips to form a releasable bond therewith and the obverse surface is provided with an indicia designating the center line of said locating strip; and
d.
e. an optional compressive pad to be positioned between said at least one elastomeric strap and the chest wall over the site of median sternotomy;
f.

16. The kit of claim 15 wherein said fastener receiving material comprises a plurality of hooks and said fasteners comprise a plurality of corresponding loops or pile portions, wherein said hooks and loops mate for form a fastener pair.

17. The method of claim 15, wherein anchor strips are provided with a curvilinear perimeter that conforms to the contours of a chest wall and have a length of about 4 to 12 inches and a width of about 1 to 5 inches, more preferably a length of about 4 to 8 inches and a width of about 1.5 to 4 inches, while said at least one elastomeric strap is formed from an elastomeric fabric comprising about 88% polyester and about 12% rubber and has a length of about 4 to 12 inches and a width of about 1 to 4 inches, more preferably a length of about 5 to 10 inches and a width of about 1.5 to 3 inches.

* * * * *

UNITED STATES PATENT AND TRADEMARK OFFICE
CERTIFICATE OF CORRECTION

| | | |
|---|---|---|
| PATENT NO. | : 8,038,634 B2 | |
| APPLICATION NO. | : 12/341546 | |
| DATED | : October 18, 2011 | |
| INVENTOR(S) | : Rolnick et al. | |

It is certified that error appears in the above-identified patent and that said Letters Patent is hereby corrected as shown below:

At column 10, line 29, claim 17 should read "The kit of claim 15".

Signed and Sealed this
Fifteenth Day of November, 2011

David J. Kappos
*Director of the United States Patent and Trademark Office*